United States Patent

Altiparmakian et al.

[11] 3,932,414
[45] Jan. 13, 1976

[54] ACRIDONE COMPOUNDS

[75] Inventors: Rodolf Altiparmakian, Binningen; Hans Bohler, Rheinfelden, AG, both of Switzerland

[73] Assignee: Sandoz Ltd., (Sandoz AG), Basel, Switzerland

[22] Filed: Apr. 1, 1974

[21] Appl. No.: 456,629

[30] Foreign Application Priority Data

Apr. 6, 1973 Switzerland.................. 5028/73

[52] U.S. Cl............... 260/279 R; 260/155; 106/23; 106/193 P; 106/288 Q; 117/132 R; 117/167; 260/37 P; 260/42.21

[51] Int. Cl.²................. C09B 15/00; C07D 219/08

[58] Field of Search...... 260/279 R, 155; 106/288 Q

[56] References Cited
UNITED STATES PATENTS 2,503,899    4/1950    Britton et al.................. 260/279 R

OTHER PUBLICATIONS

Fieser et al., "Advanced Organic Chemistry," Reinhold Publishing Corp., N.Y., (1961), pp. 626–637.
Burdeska et al., Chemical Abstracts, Vol. 78, No. 4, 17,591b, Jan. 29, 1973.

*Primary Examiner*—Nicholas S. Rizzo
*Assistant Examiner*—Diana G. Rivers
*Attorney, Agent, or Firm*—Gerald D. Sharkin; Richard E. Vila; Joseph J. Borovian

[57] ABSTRACT

Disclosed are pigments of formula I

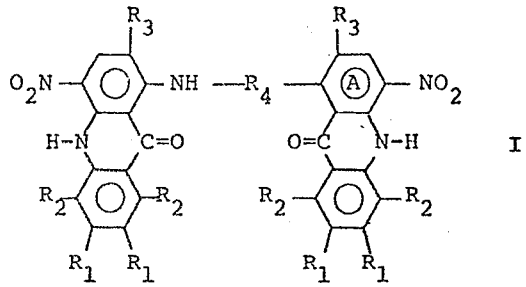

in which
the $R_1$'s, independently, each signify hydrogen, halogen, nitro, cyano, methyl, alkoxy, aminocarbonyl, alkylcarbonylamino, benzoylamino, phenylaminocarbonyl, alkylamino or phenylamino,
the $R_2$'s, independently, each signify hydrogen, halogen or methyl,
the $R_3$'s, independently, signify hydrogen or halogen, and
$R_4$ signifies a direct bond or a group $-R_5-NH-$, in which the imino group is bound to nucleus A, and $R_5$ signifies a 1,3- or 1,4-phenylene radical, unsubstituted or substituted by up to two substituents selected from halogen, methyl, alkoxy and nitro; or a radical

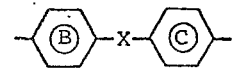

in which X signifies a direct bond, $-O-$, $-SO_2-$, $-N=N-$ or $-NHCO-$ and rings B and C are unsubstituted or substituted by up to two substituents selected from halogen, methyl, alkoxy and nitro, and their use in pigmenting synthetic plastics and resins and paper and as colorants in surface coating media such as paints, lacquers and printing inks.

16 Claims, No Drawings

ACRIDONE COMPOUNDS

The invention relates to acridone compounds.

The invention provides compounds of formula I,

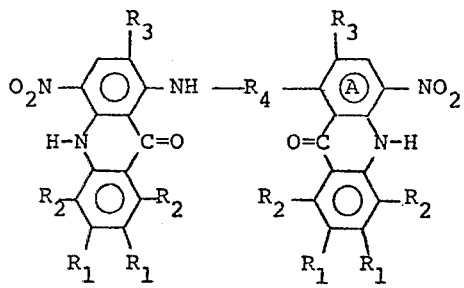

I in which
- the $R_1$'s, independently, each signify hydrogen, halogen, nitro, cyano, methyl, alkoxy, aminocarbonyl, alkylcarbonylamino, benzoylamino, phenylaminocarbonyl, alkylamino or phenylamino,
- the $R_2$'s, independently, each signify hydrogen, halogen or methyl,
- the $R_3$'s, independently, signify hydrogen or halogen, and
- $R_4$ signifies a direct bond or a group $-R_5-NH-$, in which the imino group is bound to nucleus A, and $R_5$ signifies a 1,3- or 1,4-phenylene radical, unsubstituted or substituted by up to two substituents selected from halogen, methyl, alkoxy and nitro; or a radical

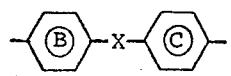

in which X signifies a direct bond, $-O-$, $-SO_2-$, $-N=N-$ or $-NHCO-$ and rings B and C are unsubstituted or substituted by up to two substituents selected from halogen, methyl, alkoxy and nitro,
and mixtures thereof.

By "halogen," as used herein, is to be understood fluorine, chlorine or bromine, chlorine and bromine being the preferred halogens.

Any alkyl or alkoxy radical or moiety in the compounds of formula I, unless otherwise stated, is preferably of 1, 2, 3 or 4 carbon atoms, more preferably of 1 or 2 carbon atoms.

In the compounds of formula I, the $R_1$'s, independently, preferably signify hydrogen, methyl, chlorine or bromine. The $R_2$'s, independently, preferably signify hydrogen or methyl, more preferably hydrogen. The $R_3$'s, independently, preferably signify hydrogen, chlorine or bromine. $R_4$ preferably signifies a direct bond, or $-R_5-NH-$, in which $R_5$ signifies a 1,3- or 1,4-phenylene radical or a 4,4'-diphenylene radical, which phenylene radical or radicals, independently, are unsubstituted or substituted by up to two substituents selected from chlorine, bromine, methyl, nitro, methoxy or ethoxy; or a group

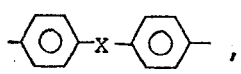

in which X signifies $-O-$, $-SO_2-$, $-N=N-$ or $-NH-CO-$.

The preferred compounds of formula I are the compounds of formula I',

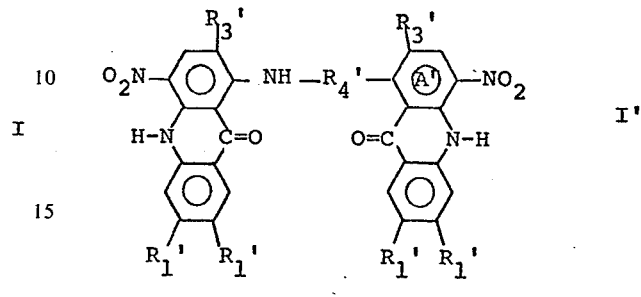

I' in which
- the $R_1'$'s, independently, each signify hydrogen, chlorine, bromine, methyl or methoxy,
- the $R_3'$'s, independently, each signify hydrogen, chlorine or bromine, and
- $R_4'$ signifies a direct bond or $-R_5'-NH-$, in which the imino group is bound to ring A', and $R_5'$ signifies a 1,4-phenylene or 4,4'-diphenylene radical, which phenylene radical in the 2 and 5 positions and which diphenylene radical in the 3 and 3' positions bears a substituent selected from chlorine, bromine, methyl, methoxy, ethoxy and nitro,
and mixtures thereof.

Further preferred compounds of formula I are the compounds of formula I'',

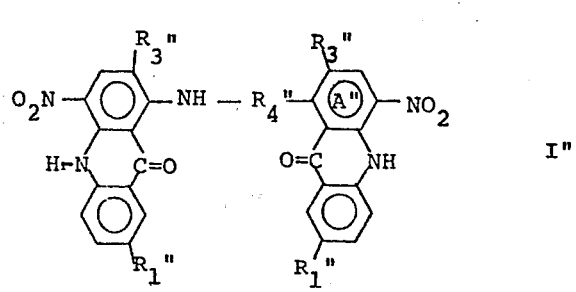

I'' in which
- the $R_1''$ 's, independently, each signify hydrogen, chlorine, bromine or methyl,
- the $R_3''$ 's, independently, each signify hydrogen, chlorine or bromine, and
- $R_4''$ signifies a direct bond or

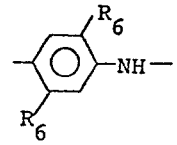

in which the imino group is bound to ring A'', and the $R_6$ 's, independently, signify chlorine or bromine, and mixtures thereof.

In the compounds of formula I'', the $R_6$ 's are preferably the same.

The invention also provides a process for the production of compounds of formula I, and mixtures thereof, characterised by a. condensing a compound of formula II,

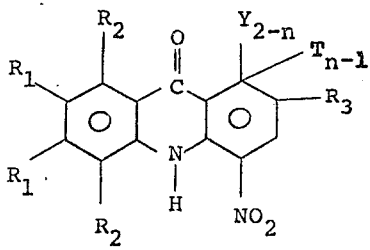

in which
the $R_1$'s, $R_2$'s and $R_3$ are as defined
Y signifies an amino group,
T signifies chlorine or bromine, and
n signifies 1 or 2,
or a mixture thereof, with a compound of formula III,

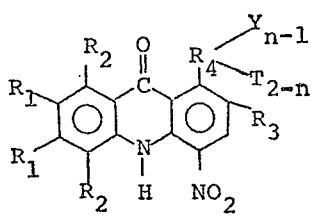 III in which the $R_1$'s, $R_2$'s, $R_3$, $R_4$, Y, T and n are as defined above, or a mixture thereof, or b. obtaining a compound of formula I, in which $R_4$ is other than a direct bond, or a mixture thereof, by condensing a compound of formula II, above, wherein n signifies 2, or a mixture thereof, with a compound of formula IV, $$R_{4a}(NH_2)_2 \quad\quad IV$$

in which $R_{4a}$ has the same significance as $R_4$, above, other than a direct bond, or a mixture thereof.

In process (a), the compounds of formula II and III are preferably condensed in the mol ratio of 1:1. Where, in the compounds of formula III, $R_4$ signifies other than a direct bond, n, in the compounds of formulae II and III, preferably signifies 2.

In process (b), the compounds of formula II are preferably condensed with the compounds of formula IV in the mol ratio 2:1.

The condensation reaction involved in processes (a) and (b) may be carried out in conventional manner. Thus, they are preferably carried out in an organic solvent, such as in a xylene mixture or in nitrobenzene. A suitable reaction temperature is from 120° to 240°C, preferably from 160° to 210°C. The reactions are preferably carried out in the presence of a basic condensation agent or acid binding agent, e.g. sodium or potassium carbonate or bicarbonate.

As will be appreciated, where mixtures of starting materials are employed, the resulting compounds of formula I will be in corresponding mixture form, and when pure starting materials are employed, the resulting compounds of formula I will be obtained in corresponding pure form. Mixtures of compounds of formula I may alternatively be obtained by simple admixture of two or more compounds of formula I.

The resulting compounds of formula I or mixtures thereof may be isolated and purified in conventional manner.

The compounds of formulae II, III and IV are either known or may be obtained in conventional manner from available starting materials.

The compounds of formula I and mixtures thereof are useful as pigments, particularly after conditioning by conventional methods for pigments.

They are suitable for pigmenting synthetic plastics and resins in the mass, with or without the use of solvents. The compounds may be incorporated in the mass in conventional manner and in conventional amounts, depending on the effect required. As examples of synthetic plastics and resins may be given polyethylene, polypropylene, polystyrene, polyvinylchloride and synthetic latices and poromerics (synthetic leathers).

They are also suitable for spin dyeing of viscose rayon, polyacrilonitrile, aromatic polyesters and cellulose acetate, again being employed in conventional manner and in conventional amounts.

Further, they are suitable for use as colourants in surface coating media, whether of an oil, water or solvent basis, such as lacquers and printing inks, again being incorporated therein in conventional manner and in conventional amounts.

Still further, they are suitable for use in conventional manner in the coating and printing of textiles and for dyeing paper in the stock prior to sheet formation.

The pigment effects produced using the compounds of formula I or mixtures thereof have notable migration and light fastness properties, good fastness to overspraying and solvents, good transparency and heat stability and good distribution properties in plastics in the mass.

The invention is illustrated by the following Examples, in which all parts and percentages are by weight and the temperatures in degrees centigrade.

EXAMPLE 1

11 Parts of 1-chloro-4-nitroacridone, 10.2 parts of 1-amino-4-nitroacridone and 7.2 parts of potassium carbonate are heated to 186° in 145 parts of nitrobenzene over the course of 1 hour while stirring. After cooling to approximately 50° the orange coloured crystals are filtered off, washed first with nitrobenzene, subsequently with ethanol and boiled for a short period in 200 parts of water in order to free them from inorganic impurities. Then they are filtered off again, washed with water and dried. The dye of formula

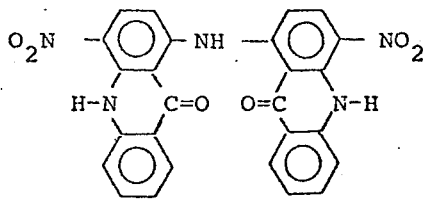

is obtained. In order to improve the pigment properties it is boiled in 60 parts of dimethyl formamide over the course of 30 minutes. After cooling to 100° the dye is filtered, washed first with hot dimethyl formamide, then with alcohol and finally dried.

EXAMPLE 2

5.5 Parts of 1-chloro-4-nitroacridone, 1.8 parts of 2,5-dichloro-1,4-phenylene diamine and 3.6 parts of potassium carbonate are heated to 200° in 60 parts of nitrobenzene over the course of approximately 1 hour while stirring. The process is continued as described in Example 1. Thus, the red crystalline pigment of formula

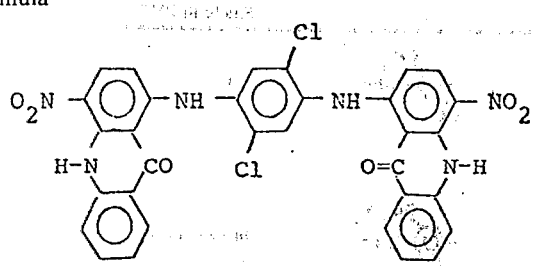

is obtained. It pigments plastics and lacquers in red shades which have very good light fastness, heat stability and migration resistance.

In the following Table further dyes of formula Ic

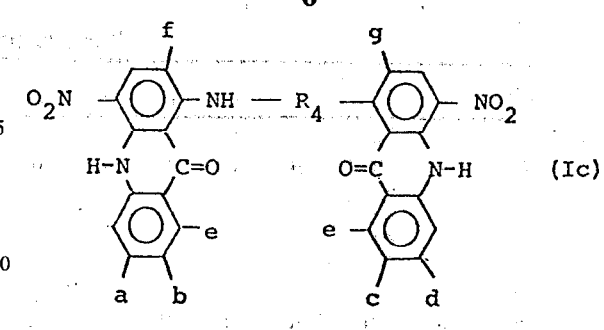

and the shades of their sample dyeings in polyvinyl chloride are indicated. The dyes are produced in analogy with the process described in Example 1 or 2.

Table

| Exp. No. | a | b | c | d | e | f | g | $R_4$ | Shade in PVC |
|---|---|---|---|---|---|---|---|---|---|
| 3 | H | —CH₃ | H | H | H | H | H | direct bond | orange |
| 4 | H | H | H | H | H | —Cl | H | do. | do. |
| 5 | H | —CH₃ | H | H | H | —Cl | H | do. | do. |
| 6 | H | do. | —CH₃ | H | H | H | H | 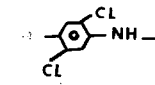 | red |
| 7 | H | do. | do. | H | H | —Cl | —Cl | do. | do. |
| 8 | H | H | H | H | H | H | do. | orange | |
| 9 | —Cl | —Cl | —Cl | CH₃ —Cl | H | H | H | do. | reddish brown |
| 10 | H | CH₃ | H | H | H | —Br | H | direct bond | orange |
| 11 | —Cl | H | H | —Cl | H | H | H | 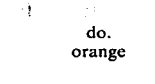 | yellowish brown |
| 12 | H | —Br | —Br | H | H | H | H | 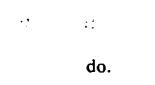 | brown |
| 13 | H H H | H —Br H | H —Br —Br | H H H | H H H | H H H | H H H | 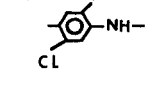 | red |
| 14 | H | H | H | H | H | —Cl | —Cl | do. | brown |
| 15 | H | H | H | H | H | —Br | —Br | do. | do. |
| 16 | H | H | H | H | H | H | H | 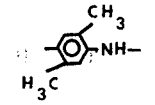 | orangestichig brown |
| 17 | H | H | H | H | H | H | H | 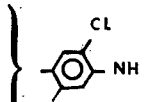 | do. |
| 18 | H | H | H | H | H | H | H | 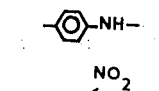 | yellowish orange |

Table-continued
| Exp. No. | a | b | c | d | e | f | g | R₄ | Shade in PVC |
|---|---|---|---|---|---|---|---|---|---|
| 19 | H | H | H | H | H | H | H | 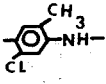 | do. |
| 20 | H | H | H | H | H | H | H | 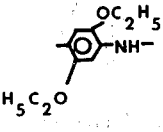 | brown-violet |
| 21 | H | H | H | H | H | H | H | 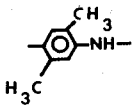 | yellowish red |
| 22 | H | H | H | H | H | H | H | 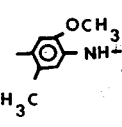 | reddish brown |
| 23 | H | H | H | H | H | H | H |  | yellow |
| 24 | H | H | H | H | H | H | H |  | do. |
| 25 | H | H | H | H | H | H | H |  | do. |
| 26 | H | H | H | H | H | H | H | 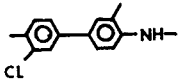 | yellowish red |
| 27 | H | H | H | H | H | H | H | 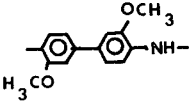 | reddish brown |
| 28 | H | H | H | H | H | H | H | 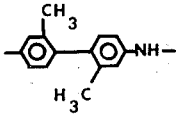 | yellow |
| 29 | H | H | H | H | H | H | H | 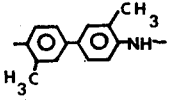 | yellowish red |
| 30 | H | H | H | H | H | H | H | 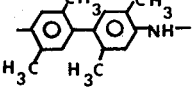 | greenish yellow |

Table-continued

| Exp. No. | a | b | c | d | e | f | g | R₄ | Shade in PVC |
|---|---|---|---|---|---|---|---|---|---|
| 31 | H | H | H | H | H | H | H | (2,4-dichlorophenyl)-phenyl-NH– | reddish yellow |
| 32 | H | H | H | H | H | H | H | –C₆H₄–SO₂–C₆H₄–NH– | greenish yellow |
| 33 | H | H | H | H | H | H | H | –C₆H₄–O–C₆H₄–NH– | yellow |
| 34 | H | H | H | H | H | H | H | –C₆H₄–N=N–C₆H₄–NH– | reddish yellow |
| 35 | H | H | H | H | H | H | H | –C₆H₄–NH–CO–C₆H₄–NH– | yellow |
| 36 | H | H | H | H | H | H | H | –(2,4-dinitrophenyl)–C₆H₄–NH– | red |
| 37 | H | –CH₃ | –CH₃ | H | H | H | H | –(2,5-dibromophenyl)–NH– | red |

APPLICATION EXAMPLE

Two Parts of the pigment of Example 1, saltground in accordance with conventional methods, are ground in a ball mill over the course of 24 hours with 48 parts of a lacquer of the following composition:

43.88 parts of a 60% solution of alkyd-melamine formaldehyde resin in xylene,
17.18 parts of a 65% melamine resin solution in butanol,
4.57 parts of butanol,
31.37 parts of xylene and
7 parts of ethyl glycol acetate.

The lacquer containing the pigment is separated from the balls by means of a nylon filter, and an aluminium sheet (on cardboard) is sprayed with this "full shade mixture". The sheet sprayed in this way is allowed to dry in the air for 15 minutes and then stoved 30 minutes at 140°. The orange coloured film thus obtained shows good light and migration fastness.

What is claimed is:
1. A compound of formula I,

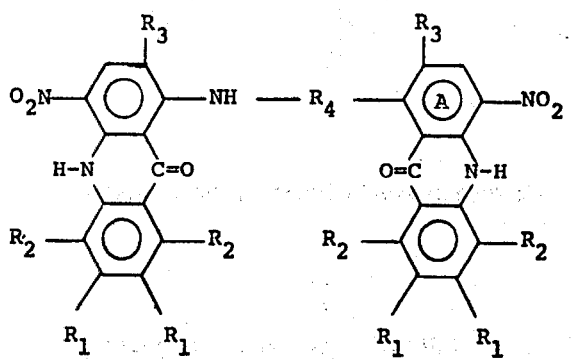

wherein the
R₁'s are independently hydrogen, $C_{1-4}$ alkyl, $C_{1-4}$ alkoxy, chlorine or bromine,
the R₂'s are independently hydrogen, methyl, chlorine or bromine,
the R₃'s are independently hydrogen, chlorine or bromine, and
R₄ is a direct bond or a group —R₅—NH—, in which the imino group is bound to nucleus A, and R₅ is a 1,3- or 1,4-phenylene radical, unsubstituted or substituted by 1 or 2 substituents selected from chlorine, bromine, methyl, $C_{1-4}$ alkoxy and nitro; or a radical

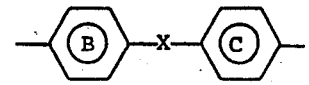

in which X is a direct bond, —O—, —SO₂—, —N=N—, or —NHCO— and each of rings B and C is optionally substituted by 1 or 2 substituents selected from chlorine, bromine, methyl, $C_{1-4}$ alkoxy and nitro,
or a mixture of compounds of formula I.

2. A compound or mixture of compounds of claim 1, wherein the $R_1$'s are independently, hydrogen, methyl, methoxy, chlorine or bromine.

3. A compound or mixture of compounds of Claim 2, wherein the $R_1$'s are independently hydrogen, methyl, chlorine or bromine.

4. A compound or mixture of compounds of claim 1, wherein the $R_2$'s are independently hydrogen or methyl.

5. A compound or mixture of compounds of Claim 3, wherein the $R_2$'s are hydrogen.

6. A compound or mixture of compounds of claim 1, wherein $R_4$ is a direct bond or —$R_5$—NH—, where $R_5$ signifies a 1,3- or 1,4-phenylene radical; a 4,4'-diphenylene radical, which phenylene radical or radicals are each, independently, unsubstituted or substituted by up to 2 substituents selected from chlorine, bromine, methyl, nitro or $C_{1-4}$ alkoxy; or a group

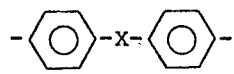

in which X is —O—, —$SO_2$—, —N=N— or —NH—CO—.

7. A compound or mixture of compounds of claim 6, and of formula I',

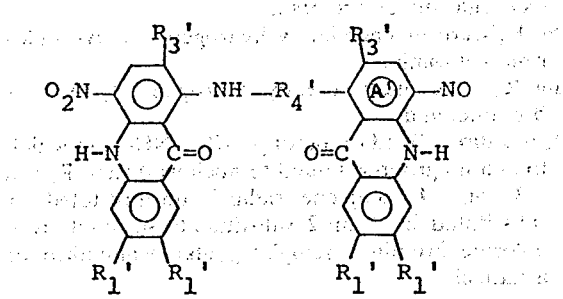

in which
the $R_1$'s are independently hydrogen, chlorine, bromine, methyl or methoxy,
the $R_3$' 's are independently hydrogen, chlorine or bromine, and
$R_4$' is a direct bond or —$R_5$'—NH—, in which the imino group is bound to ring A', and $R_5$' signifies a 1,4-phenylene or 4,4'-diphenylene radical, which phenylene radical in the 2 and 5 positions and which diphenylene radical in the 3 and 3' positions bears a substituent selected from chlorine, bromine, methyl, methoxy, ethoxy and nitro.

8. A compound or mixtures of compounds of claim 7, and of formula I",

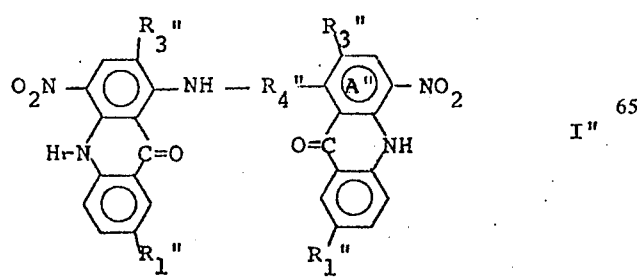

in which
the $R_1$" 's are independently hydrogen, chlorine, bromine or methyl,
the $R_3$" 's are independently hydrogen, chlorine or bromine, and
$R_4$" is a direct bond or

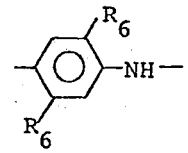

in which the imino group is bound to ring A", and the $R_6$ 's are independently, chlorine or bromine.

9. A compound or mixture of compounds of claim 8, wherein the $R_6$'s are the same.

10. A compound of claim 8 and of formula

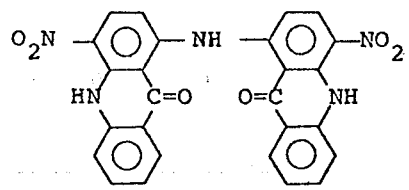

11. A compound of claim 8 and of formula

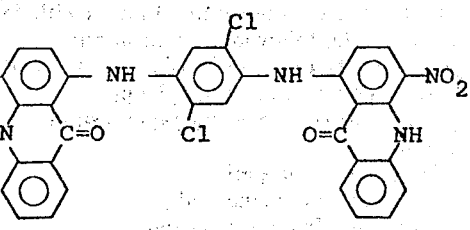

12. A compound of claim 8, and of formula

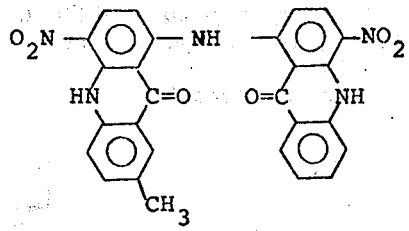

13. A compound of claim 8, and of formula

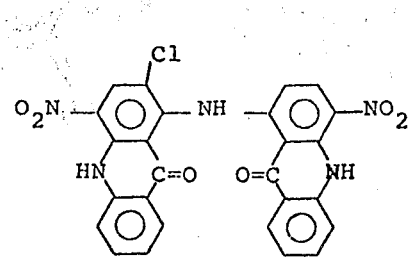

14. A compound of claim 8, and of formula
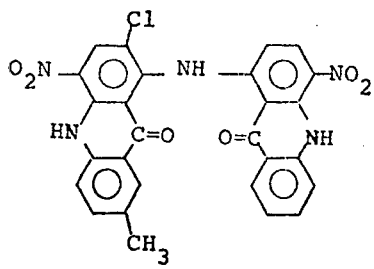
15. A compound of claim 8, and of formula
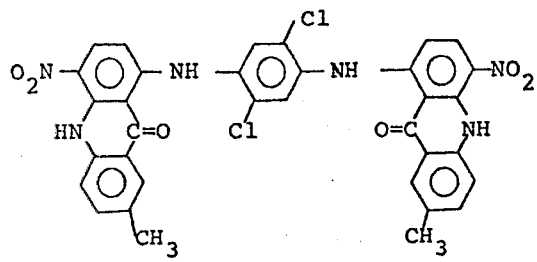
16. A compound of claim 8, and of formula
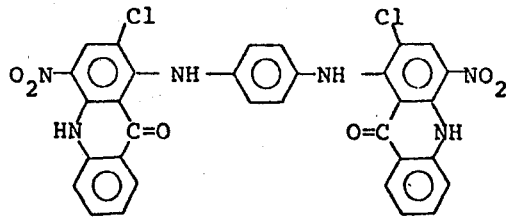
* * * * *